US00PP37654P2

(12) United States Plant Patent
Pomper et al.

(10) Patent No.: US PP37,654 P2
(45) Date of Patent: Sep. 1, 2026

(54) PAWPAW TREE NAMED 'Hi 7-1'

(50) Latin Name: ***Asimina triloba* (L.) Dunal.**
Varietal Denomination: Hi 7-1

(71) Applicant: Kentucky State University, Frankfort, KY (US)

(72) Inventors: Kirk Pomper, Frankfort, KY (US); Sheri Crabtree, Frankfort, KY (US); Jeremy Lowe, Frankfort, KY (US)

(73) Assignee: Kentucky State University, Frankfort, KY (US)

( * ) Notice: Subject to any disclaimer, the term of this patent is extended or adjusted under 35 U.S.C. 154(b) by 0 days.

(21) Appl. No.: 19/314,949

(22) Filed: Aug. 29, 2025

(51) Int. Cl.
*A01H 5/08* (2018.01)
*A01H 6/00* (2018.01)

(52) U.S. Cl.
USPC ..... Plt./156
CPC ..... *A01H 6/00* (2018.05); *A01H 5/08* (2013.01)

(58) Field of Classification Search
USPC ..... Plt./156
CPC ..... A01H 5/08; A01H 5/00; A01H 6/00
See application file for complete search history.

(56) References Cited

PUBLICATIONS

Behrends et al. Comparison of Grafting and Budding Propagation Techniques for Cultivars of the North American Pawpaw, HortTechnology Dec. 2024 34(6), 653-657. (Year: 2024).*
England's Orchard and Nursery 2024, retrieved on Oct. 15, 2025 at https://www.nuttrees.net/England's%20Orchard%20and%20Nursery%20-%20Scion%20list%202024.pdf, pp. 1, 21. (Year: 2024).*
Facebook Pawpaw Fanclub International, retrieved on Oct. 15, 2025 at https://www.facebook.com/groups/pawpawfanclubinternational/posts/24142877748732536/, 6 pp. (Year: 2025).*
Peaceful Heritage, KSU Dunnigan TM Pawpaw Tree (KSU 7-1), retrieved on Oct. 15, 2025 at https://peacefulheritage.com/products/ksu-dunnigan-pawpaw-tree-peaceful-heritage-nursery, 4 pp. (Year: 2025).*

* cited by examiner

*Primary Examiner* — June Hwu
(74) *Attorney, Agent, or Firm* — Patrick M. Torre; Stites & Harbison PLLC

(57) ABSTRACT

This disclosure relates to pawpaw trees, and more specifically to a pawpaw tree with pyramidal growth form and moderate vigorous growth; a superior fruit distinguished by large, firm, orange-yellow fleshy fruits. The number of fruit per cluster is low, often in singles, which simplifies harvesting.

3 Drawing Sheets

GOVERNMENT INTEREST

This invention was made with partial government support under grant number 7004384 awarded by the U.S. Department of Agriculture Evans Allen Research Capacity Grant Funding. The government has certain rights in the invention.

Latin name: *Asimina triloba* (L.) Dunal.
Variety denomination: 'Hi 7-1'.

BACKGROUND

This disclosure is directed to a new and distinct variety of pawpaw tree. It was discovered by the applicant in September 2011 as part of a pawpaw breeding program to develop new varieties with high fruit quality. The species *Asimina triloba* (L.) Dunal or pawpaw, is the largest native edible fruit of North America, a member of the Annonaceae family. The present variety, named 'Hi 7-1', is a distinct variety of pawpaw which represents an improvement over existing pawpaw varieties because of higher yields and superior flavor, and a high grafting and budding propagation success rate. Additionally, the fruit has a percent seed that is only 8.0% of fruit weight.

BRIEF SUMMARY

This new cultivar is a seedling grown from improved seed that contained a collection of 28 improved selections and commercially available cultivars. The parents are unknown. The original tree is a seedling from mixed seed collected from a pawpaw regional variety trial planted in 1998. Propagated trees were grafted onto pawpaw seedling rootstock of unknown parentage. This new cultivar is 'Hi 7-1.' The seedling was germinated, grown out in greenhouses in 2002,and planted in an orchard in 2004. Following discovery and asexual reproduction by grafting and budding, it was further tested as selection 'Hi 7-1'. In a 2016 experiment, 'Hi 7-1' was compared to 'Hi 1-4' (U.S. Plant patent application Ser. No. 19/314,990), KSU-Atwood™, KSU-Benson™, KSU-Chappell™, G6-120, G9-111, G4-25, G5-23, Hy3-120, and G9-109 for grafting and budding propagation success rate. 'Hi 7-1' had a 50% propagation success rate for whip-and-tongue grafting, cleft grafting, and chip bidding techniques, which was higher than for the selection KSU-Benson™. Studies have demonstrated that orchard-grafted 'Hi 7-1' trees are capable of producing fruit within several years after grafting, allowing growers to rapidly transition existing orchards to this selection.

The variety is most notable for large size, pleasing yellow orange pulp, and a mild tropical like flavor that is a blend of banana, pineapple, and mango. Fruit will store at 36° F. for approximately 3 weeks and maintain without atmosphere modification. The fruit of 'Hi 7-1' has been rated superior to fruit of pawpaw varieties of Sunflower, TALLAHATCHIE, and KSU-Benson™ by sensory evaluation panels for flavor tests (Tables 1 and 2). As shown in Tables 1 and 2, 'Hi 7-1' showed a better flesh-to-seed ratio, larger fruit size, higher yields, and better flavor in taste tests compared to the other pawpaw varieties compared. The average optimum harvest date is during the first week of September, approximately 5 days after KSU-Benson™. The fruit on a tree ripens over a three week harvest period.

This new variety is also characterized by a moderately vigorous tree with a pyramidal growth habit if left unpruned. Trees bear fruit annually and usually do not require hand thinning. The variety has been hardy in the field at the above-noted location at Frankfort, Kentucky, with trees showing little winter injury and bearing fruit annually.

The fruit pulp is sweet with a juicy texture, with a low-acid flavor and moderate aroma. The skin is green in coloration. The pulp flesh is color is yellow-orange and soft. The fruit usually contains 10-16 seeds that are dark brown in color.

This new cultivar has been asexually reproduced by means of grafting and budding in Frankfort, Kentucky. Examination of various trees of the cultivar has confirmed that the combination of characteristics described herein are firmly fixed through successive generations.

BRIEF DESCRIPTION OF THE DRAWINGS

This new variety of pawpaw tree is illustrated by the accompanying photographic drawings depicting the plant by the best possible color representation, wherein.

All photographs were taken in September in Frankfort, Kentucky.

DETAILED BOTANICAL DESCRIPTION

The following observations are believed to be characteristic of this cultivar and in combination, distinguish this pawpaw tree as a new and distinct cultivar.

Figure 1:
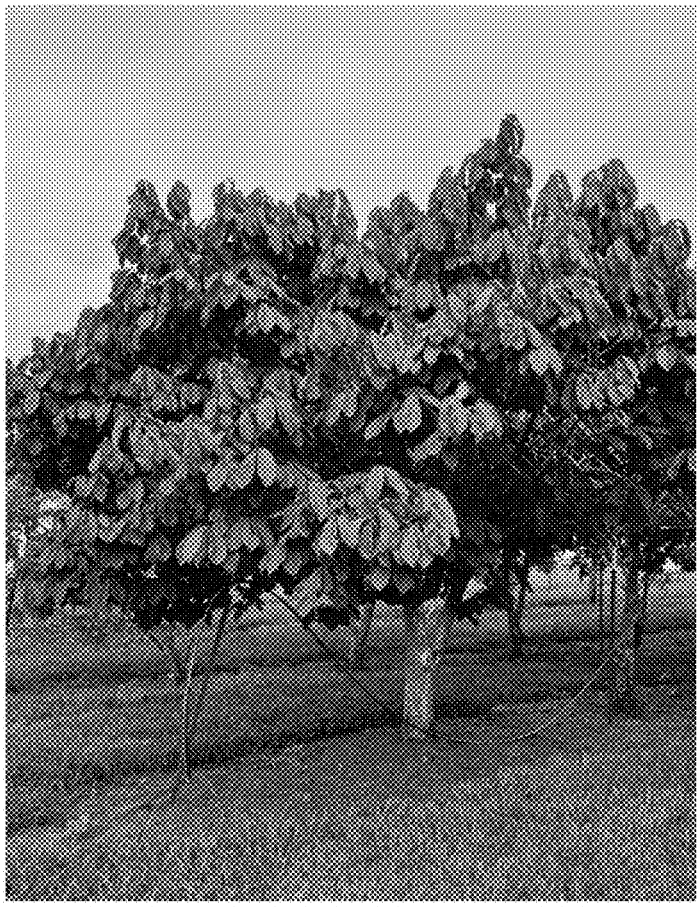
FIG. 1 is a photographic print in full color showing the form of a mature tree (21 years old) and the ripening fruit.
Figure 2:
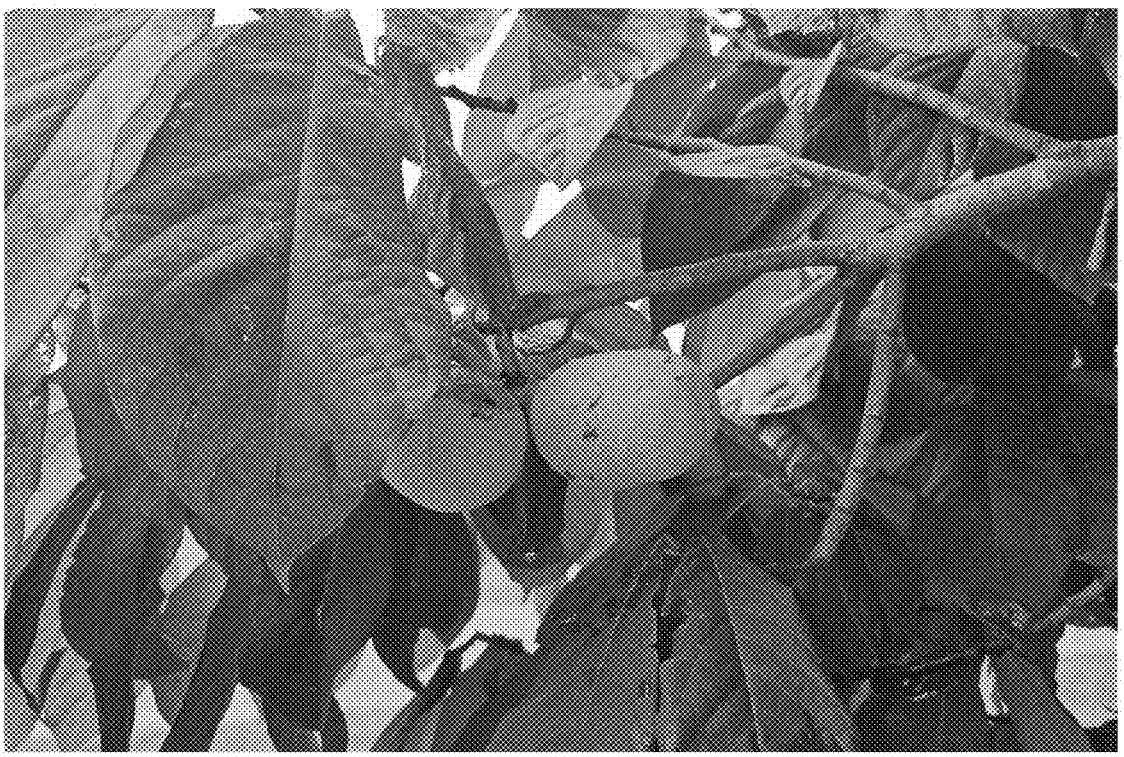
FIG. 2 is a photographic print in full color showing the maturing fruit on a section of the tree.
Figure 3:
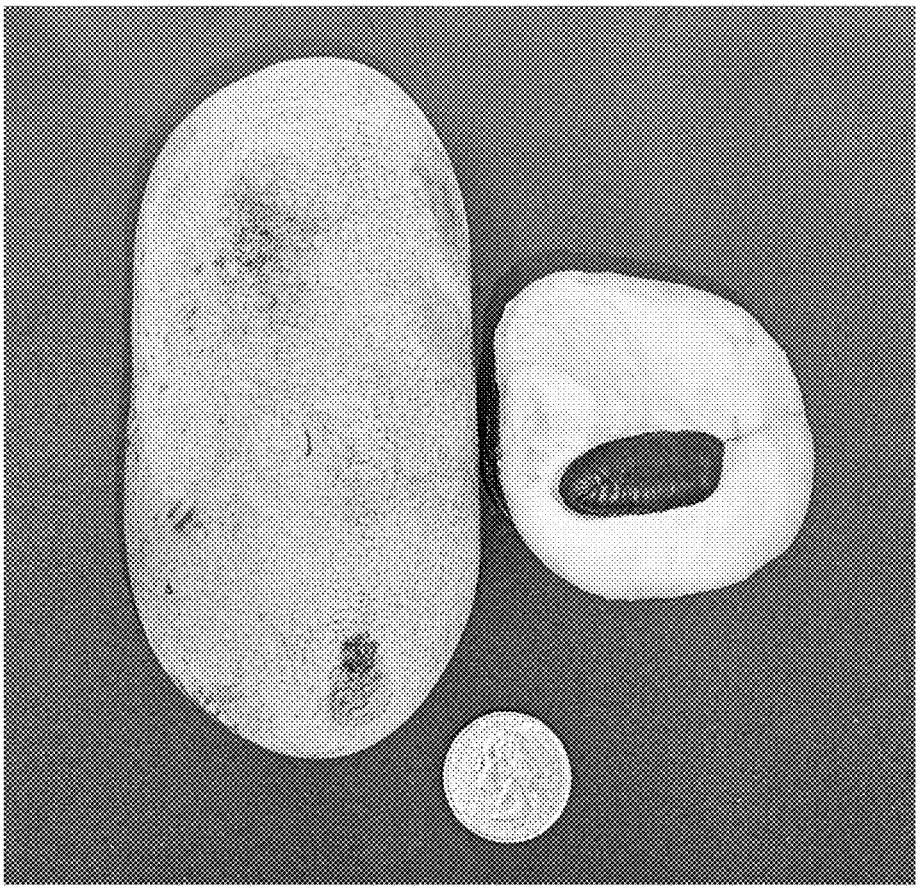
FIG. 3 is a photographic print in full color showing the fruit of this cultivar.

Tree (see FIG. 1; depicted tree is 21 years old):

*Size.*—Medium. 5-6 m on its own roots but taller on more vigorous seedling rootstock at maturity. The plant cannot be propagated by cuttings. It is propagated by grafting or budding onto seedling rootstock. Average spread is 4.5 meters. The bark is smooth with wart-like lenticels having a light grey-grown color RHS 197D or 196A (Royal Horticultural Colour Chart (R.H.S.) 2015, London, G.B. Sixth Ed.) Terminal buds are 0.85-1.3 cm long, naked (no scales), dark brown, and pubescent. Axillary buds are 0.42-0.85 cm long, narrow, pointed, naked (no scales), and covered with a dark brown pubescence (color RHS 165A or 200B).

*Vigor.*—Medium when grafted onto seedling root stock. United States Department of Agriculture (USDA) Plant Hardiness Zones are 5-8; the tree is hardy to at least −28° C.

*Habit.*—Pyramidal to rounded with age.

*Branching pattern.*—Spreading. Crotch angles wide. Branches widely spaced.

*Apical dominance.*—Medium.

Leaves:

*Shape.*—Oblanceolate with acuminate tip and attenuate to the base, as is typical for the species. Average ratio of length to width to is 2.3.

*Size.*—Measurements are from mature leaves attached at midpoint of actively growing shoots of current season's growth. Average size is 9.8 cm wide, 21.6 cm long.

*Color.*—Upper surface varies from R.H.S. Green 139B to R.H.S. Green 141A. Lower Surface R.H.S. Green 139D. Fall color is golden yellow (RHS 2A or 3B). Both colors typical for the species.

*Aspect.*—Slightly drooping when grown in full sun, as is typical for the species.

*Arrangement.*—Alternate opposite (leaf arrangement is opposite).

*Surface texture.*—Glabrous on the upper surface, and glabrous to slightly pubescent on veins on the lower surface, with a cuneate base and acute midrib. Margins are entire. Leaf venation is pinnate.

*Petiole.*—Color green similar to lower leaf surface. Average diameter 2.9 mm at the petiole mid-point. Length had an average of 7.5 mm.

Flower:

*Size.*—Medium to Small. As the flower matures from female to male stage over several days. Size of the female stage flower-Diameter 25 to 30 mm average. Size of the male stage flower-Diameter 30-40 mm average. Blooming season is spring (early April to mid-May in Kentucky). Flowers have a globular androecium, early stage beige (RHS 164D), late stage brown (RHS 200A or 200B), and a gynoecium light green (RHS 142A), usually composed of 3-7 carpels.

*Color.*—Maroon. R.H.S. Red 45A at maturity with upper and lower surfaces of the petals the same color. Flowers have an inner and outer whorl of three petals each and three sepals. Petals 2.0-2.5 cm long and 1.5 cm wide. Sepals are 25-50 mm in diameter, color light-medium green with grown pubescence (RHS 151B, 151C, 154A, or 154B).

The variety may produce up to 5% fruit set with self-pollination in controlled pollination tests, but cross pollination is desirable for commercial production.

Fruit:

*Dates of picking.*—Mid Season, generally from September 1 to 20 at Frankfort, Kentucky; however, dates can vary by more than a week depending on the degree of drought, high rainfall, and summer heat.

*Cluster size or fruit number.*—Average 2.5 fruit per cluster over a three-year period.

Fruit Shape.—From broadly ellipsoidal to somewhat cylindrical with rounded ends. Shape varies greatly.

*Fruit size.*—Fruit is large, averaging 181 g, with 2.5 fruit per cluster over a three-year period.

*Skin color.*—Under-ripe fruit pale green ranging from R.H.S. Green 142D to 143D. Ripe fruit pale yellowish green, R.H.S. Green 149C to 150A. After the fruit passes its climacteric peak and falls from the tree, browning of the fruit occurs cover the entire skin surface, as is typical for the species.

*Color break.*—There is a small change in the color of the fruit after it is fully ripe, however it is not a reliable indicator for hand harvesting of early ripening fruit. Color break precedes browning of the skin when it is overripe.

*Fleshiness*.—Medium to high. Percent seed is 8.0% on average over three years.

*Flesh color*.—Creamy yellow and uniform throughout. Pulp color ranges from R.H.S. Yellow-Orange 3A, 4A, and 5B.

*Seeds*.—Fruit usually contains 10-16 seeds that are dark brown in color (RHS 200A, 200B, and 200C). Average size is 3 cm long, oval to bean-shaped, having a smooth surface.

*Aroma of cut ripe fruit*.—Pleasant. Low power.

*Flavor*.—Very Sweet, Brix 25%, mild, nonbitter, and nonastringent assessed over a three-year period.

*Diseases and pests*.—Leaf spots can infect leaves and fruits include a complex of *Mycocentrospora asiminae, Rhopaloconidium asiminae,* and *Phyllosticta asminae.* Symptoms include light brown spots on leaves, and brown to black superficial spots on the fruit surface. Since the blackened skin is no longer expandable, continued fruit growth after infections can case fruit skin cracks exposing the flesh to bacteria and insects. This occurs occasionally with this cultivar. *Talponia plummeriana,* the Pawpaw Peduncle Borer, larvae can damage small numbers of flower peduncles killing some flowers. However, this has little or no impact on yield with the usual over of production of flowers on the tree.

*Storage ability*.—Ripening fruit will store at 36° F. for approximately 3 weeks and maintain eating quality without atmosphere modification.

*Use*.—The variety has excellent quality for fresh consumption and pulp extraction for value-added product use.

TABLE 1

Pawpaw advanced selection and six cultivars ranked in a fruit tasting by participants on a scale of 1 (poor) to 5 (excellent) on the basis of flavor, appearance, and texture.

| Variety | Flavor | Appearance | Texture |
|---|---|---|---|
| Hi 7-1 | 4.05 a | 4.19 a | 4.23 a |
| KSU-Atwood | 4.06 a | 3.83 bc | 3.85 bc |
| KSU-Benson | 3.57 b | 4.17 a | 3.89 bc |
| KSU-Chappell | 4.00 a | 4.13 a | 3.95 abc |
| Sunflower | 3.50 b | 3.75 c | 3.76 cd |
| Susquehanna | 4.12 a | 4.18 a | 4.10 ab |
| Tallahatchie | 3.43 b | 3.56 c | 3.46 d |
| significance | *** 0.0000 | *** 0.0000 | *** 0.0000 |

TABLE 2

| Selection | Fruit Weight(g) | Percent Seed | Brix |
|---|---|---|---|
| 2019 | | | |
| KSU-Atwood | 183.2 | 6.205 | 24.3 |
| Hi 1-4 | 246.7 | 7.00% | 26.4 |
| Hi 7-1 | 182.5 | 7.6% | 26.3 |
| 2023 | | | |
| KSU-Atwood | 238.6 | 5.90% | 26.4 |
| Hi 1-4 | 214.0 | 6.85% | 24.9 |
| Hi 7-1 | 202.0 | 7.32% | 25.8 |
| 2024 | | | |
| KSU-Atwood | 160.3 | 8.00% | 23.3 |
| Hi 1-4 | 229.7 | 5.90% | 25.9 |
| Hi 7-1 | 157.7 | 9.3% | 23.0 |

We claim:

1. A new and distinct *Asimina triloba* (L.) Dunal (pawpaw) tree named 'Hi 7-1' substantially as shown and described herein.

* * * * *